United States Patent
Rehm

(10) Patent No.: US 7,601,544 B2
(45) Date of Patent: Oct. 13, 2009

(54) METHOD AND APPARATUS FOR USING INFRARED READINGS TO DETECT MISIDENTIFICATION OF A DIAGNOSTIC TEST STRIP IN A REFLECTANCE SPECTROMETER

(75) Inventor: Gary E. Rehm, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 734 days.

(21) Appl. No.: 10/056,623

(22) Filed: Jan. 28, 2002

(65) Prior Publication Data

US 2002/0132363 A1 Sep. 19, 2002

(51) Int. Cl.
- G01N 21/00 (2006.01)
- G01N 21/77 (2006.01)
- G01N 21/47 (2006.01)
- G01N 35/00 (2006.01)
- G01N 33/72 (2006.01)

(52) U.S. Cl. .................. 436/164; 436/169; 436/46; 436/66; 356/446

(58) Field of Classification Search .............. 436/164, 436/169, 46, 66; 356/446
See application file for complete search history.

(56) References Cited

U.S. PATENT DOCUMENTS

| 5,272,518 A | 12/1993 | Vincent |
| 5,397,538 A | 3/1995 | Stark et al. |
| 5,426,289 A | 6/1995 | Kinoshita et al. |
| 5,500,375 A | 3/1996 | Lee-Own et al. |
| 5,605,837 A | 2/1997 | Karimi et al. |
| 5,654,803 A * | 8/1997 | Howard et al. .............. 356/446 |
| 5,661,563 A | 8/1997 | Howard et al. .............. 356/446 |
| 5,701,181 A | 12/1997 | Boiarski et al. |
| 5,728,352 A * | 3/1998 | Poto et al. ................. 422/82.05 |
| 5,877,863 A | 3/1999 | Ross et al. |
| 5,889,585 A | 3/1999 | Markart |
| 5,945,341 A * | 8/1999 | Howard, III .................. 436/46 |
| 6,261,522 B1 * | 7/2001 | Hough et al. ............. 422/82.05 |
| 6,316,264 B1 * | 11/2001 | Corey et al. ................... 436/66 |
| 6,458,596 B1 * | 10/2002 | Poellmann .................. 436/169 |

FOREIGN PATENT DOCUMENTS

| JP | 56-016826 | 2/1981 |
| JP | 02-001818 | 1/1990 |
| JP | 04-276526 | 10/1992 |
| JP | 06-242008 | 2/1994 |
| JP | 06-111040 | 4/1994 |
| JP | 08-050210 | 4/1994 |
| JP | 07-005110 | 1/1995 |
| JP | 07-098416 | 4/1995 |

(Continued)

*Primary Examiner*—Jill Warden
*Assistant Examiner*—Lore Jarrett
(74) *Attorney, Agent, or Firm*—Richard L. Sampson; Noam R. Pollack

(57) ABSTRACT

A method and apparatus for using an infrared reading to detect the misidentification of a diagnostic test strip disposed on a feed table comprising the steps of determining if the test strip possesses specified reagents, reading the infrared reflectances from the reagent positions, determining if the reflectances are within an acceptable predetermined range and aborting the test if the infrared reflectances are not within the acceptable predetermined range.

28 Claims, 6 Drawing Sheets

FOREIGN PATENT DOCUMENTS

| | | |
|---|---|---|
| JP | 08-111107 | 4/1995 |
| JP | 07-333169 | 12/1995 |
| JP | 08-509291 | 1/1996 |
| JP | 09-061131 | 4/1996 |
| JP | 08-304287 | 11/1996 |
| JP | 06-118374 | 3/1997 |
| JP | 10-132734 | 5/1998 |
| WO | WO 96/07907 * | 3/1996 |

* cited by examiner

US 7,601,544 B2

METHOD AND APPARATUS FOR USING INFRARED READINGS TO DETECT MISIDENTIFICATION OF A DIAGNOSTIC TEST STRIP IN A REFLECTANCE SPECTROMETER

FIELD OF THE INVENTION

The present invention relates to a method and apparatus for using infrared reflectance to detect the misplacement of diagnostic test strips within reflectance spectrometers.

BACKGROUND OF THE INVENTION

The use of diagnostic test strips to analyze the components in a sample of human body fluid is well known. Typically, diagnostic test strips are made of an absorbent material in which a reagent system is absorbed. The diagnostic test strips respond to the presence of a pre-selected analyte in the test fluid with a visually detectable signal such as a change in color. The change in color that appears in one or more test fields on the diagnostic test strip can be the result of an enzymatic reaction in which a redox dye is oxidized or reduced to produce the colored response.

Alternatively, the diagnostic test strip is made of a material through which the analyte and labeled antibodies specific to the analyte can flow to form analyte labeled antibody conjugates that are captured in a specific detection zone of the strip to provide a detectable response when analyte is present in the fluid sample. These devices can employ either a sandwich-type format in which the response is directly proportional to the concentration of the analyte in the test fluid or a competitive format where the intensity of the response is inversely proportional to the analyte concentration.

While the detectable response obtained using such diagnostic test strips can be observed visually to obtain a qualitative or semi-quantitative measure of the analyte in the test sample, greater quantitation and faster, more reliable handling of multiple test strips can be achieved by reading the developed test strips instrumentally, typically by using a reflectance spectrometer that determines the intensity of reflection from the test field surface.

The use of reflectance spectrometers to analyze the components in a sample of human body fluid is well known.

Conventional reflectance spectrometers have been used to detect the presence of an analyte in a urine sample disposed on a diagnostic test strip. Any analyte present in the urine reacts with the reagent on the diagnostic test strip, causing the diagnostic test strip to change color to an extent that depends on the concentration of the analyte in the urine sample. For example, in the presence of a relatively large concentration of blood, the test field on the diagnostic test strip that tests for the presence of blood in the urine sample may change in color from yellow to dark green. Conventional reflectance spectrometers determine the intensity of the reflected light in the developed diagnostic test strip by illuminating the strip with light at one angle (typically 90°), detecting the reflected light at a different angle (typically 45°) and selecting the measured color or wavelength range at either the source or detector. The signal at the detector is typically amplified, converted to digital form and analyzed by computer. Conventionally, at the beginning of the test, the operator of the device will input information via a keyboard or other means to tell the instrument the analyte that the particular strip is designed to test, so that the read out may be correlated with an appropriate reference. Thus, if the test were designed to determine the presence of blood in the test sample, the readout on the display would be correlated with a reference value corresponding to the presence of blood. Because of the need for operator input, the degree of automation of the operation is less than complete and various techniques have been developed to further automate the process by providing the strips with indicators from which the device can determine the analyte to which a particular test strip is directed without the need for operator intervention.

One problem with conventional reflectance spectrometers is that a misplacement of the diagnostic reagent test strip within the reflectance spectrometer adversely affects the accuracy of the results produced by the reflectance spectrometer. Misplacement of the diagnostic reagent test strip, either by tilting the strip or incompletely inserting the strip into the table, may lead to misidentification of the diagnostic test strip. Many methods have been designed in an attempt to prevent the misidentification of a strip that is inadvertently placed into the feed table incorrectly. Each of these methods does not adequately prevent misidentification of test strips. First, the percentage reflectance limits for each color band could not be tightened or narrowed because of vendor process variation and known between-instrument variation. Second, it was considered that eliminating several color bands that had reflectance limits near or next to other colored bands would sufficiently eliminate misidentification of test strips. This method marginally reduces misidentification; however, some new multiples are still analyzed as other new multiples by strip misplacement and it was shown that all new multiples can be caused to be incorrectly inspected as the default by specific improper placement. Third, it was pondered that the use of IR readings of the color bands would reduce or eliminate the misidentification problem, however, all color bands can appear "white" by the improper placement of the test strips and thus read as the default band. Further, the color bands have a large variety of IR reflectances that are virtually uncontrolled. Finally, it was considered that the use of the red, blue and green pad reflectances would eliminate the misidentification problem; however, all reagents change at the visible wavelengths due to concentration differences and thus would be unusable.

For the foregoing reasons, there exists a need for a method and apparatus to aid in detecting the misplacement of diagnostic test strips within reflectance spectrometers.

SUMMARY OF THE INVENTION

The above need is met by embodiments of the invention in one or more of the following aspects. In one aspect, the invention relates to an automated method for using infrared reflectance readings to detect the misplacement of diagnostic test strips within reflectance spectrometers by determining if the test strip possesses certain specified reagents, locating the position of these reagents on the test strip, reading the infrared percent reflectances on the test strip and determining if the reflectances are within an acceptable preset range. This method is aborted if the reflectances are not within the acceptable predetermined range of infrared reflectances. This embodiment, for example, examines, among other things, the infrared reflectances of the test strip for leukocyte, glucose and albumin reagents. The test will be aborted if the resulting reflectances are outside the predetermined range, indicating that the test strip has been misplaced more than about 0.020" from a central location on the feed table or has been incompletely inserted by more than about 0.050".

An improved spectrometer has been discovered that comprises a source of illumination for generating light rays, a support member adapted to support a reagent pad, the support member having a position in which the reagent pad is illuminated by the light rays generated by the illumination source, a reflectance detector positioned to receive light rays from the reagent pad, the reflectance detector occupying a detection area. The spectrometer further comprises a housing having an aperture formed therein, the aperture being disposed between the illumination source and the reagent pad and being adapted to cause the light rays generated by the illumination source to illuminate an area of the reagent pad, means for defining a first optical path from the illumination source to the reagent pad in which substantially all singly-reflected light rays generated by the illumination source are prevented from reaching the reagent pad. The means for defining the first optical path having a non-planar wall comprises a first wall portion with a specular reflective surface disposed to reflect substantially all of the light-rays generated by the illumination source which reach the first wall portion to an area which does not include the aperture, a second wall portion with a specular reflective surface disposed to reflect substantially all of the light rays generated by the illumination source which reach the second wall portion to an area which does not include the aperture, means for defining a second optical path from the reagent pad to the reflectance detector in which substantially all singly-reflected light rays from the reagent pad are prevented from reaching the reflectance detector, the means for defining the second optical path having a non-planar wall comprising a third wall portion with a specular reflective surface disposed to reflect substantially all of the light rays which reach the third wall portion from the reagent pad to an area which does not include the detection area and a fourth wall portion with a specular reflective surface disposed to reflect substantially all of the light rays that reach the fourth wall portion from the reagent pad to an area which does not include the detection area. The spectrometer is further able to measure the infrared analyses referred to above, determine if the test strips have been improperly inserted, and report an error and abort the test if it is determined that the test strip has been improperly inserted.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

Other objects and advantages of the invention will become apparent upon reading the following description of illustrative embodiments and upon reference to these drawings.

Figure 1:
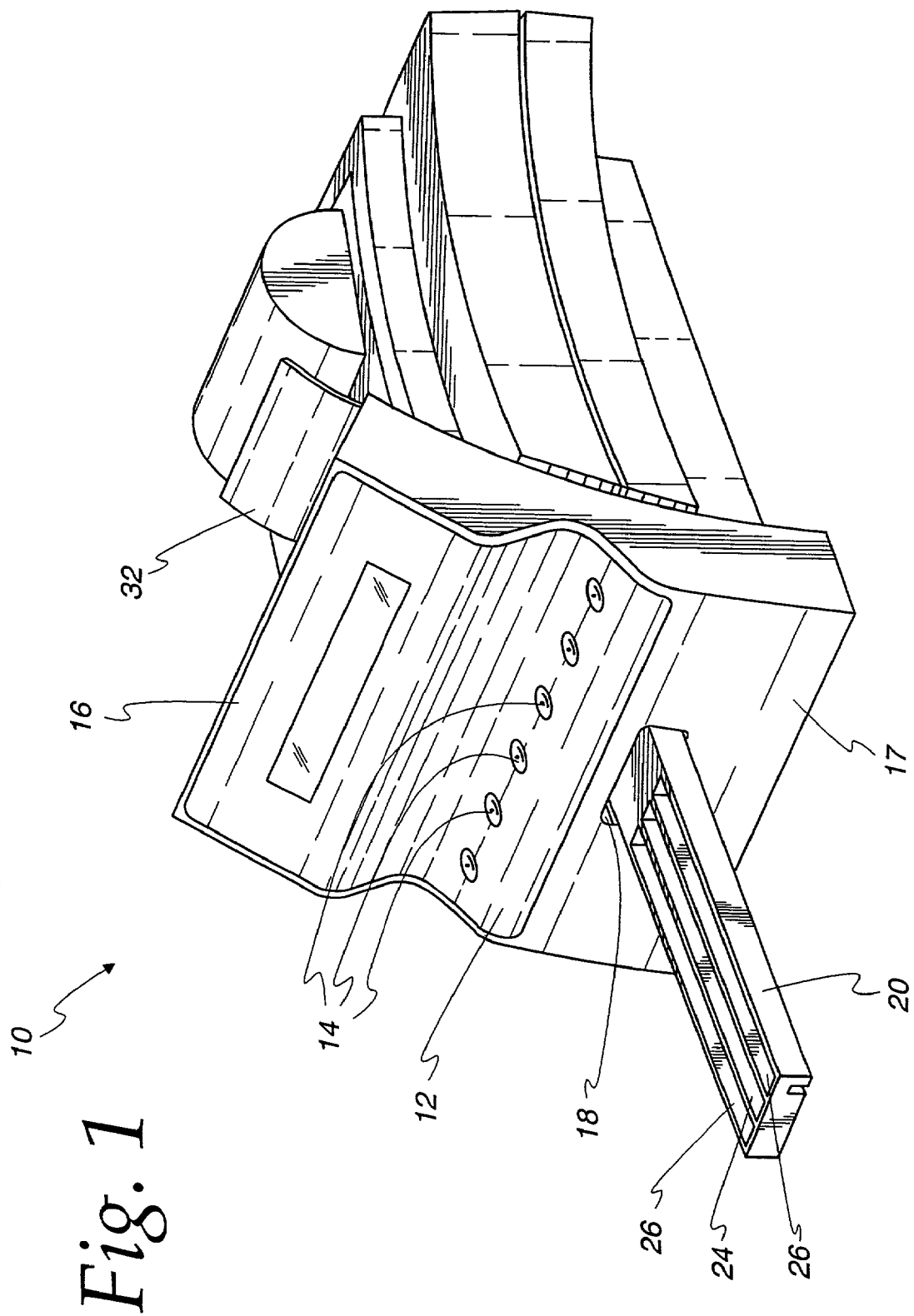
FIG. 1 is a perspective view of a reflectance spectrometer that may be used to perform various tests of a body fluid sample disposed on a diagnostic test strip.

While the invention is susceptible to various modifications and alternative forms, specific embodiments thereof have been shown by way of example in the drawings and will herein be described in detail. It should be understood, however, that the drawings are not intended to limit the invention to the particular forms disclosed, but on the contrary, the invention is to cover all modifications, equivalents and alternatives that fall within the spirit and scope of the invention

DESCRIPTION OF EMBODIMENTS OF THE INVENTION

To overcome the problems listed above that occur when a diagnostic test strip is misplaced, a method to aid in detecting the misplacement of diagnostic test strips within reflectance spectrometers has been discovered. Specifically, the spectrometer is programmed to determine the presence of several reagents, including leukocyte, glucose and albumin. After this determination, the spectrometer must determine if these reagents are located in the proper locations on the test strip. Assuming affirmative responses are obtained to the previous two inquiries, the spectrometer compares the percent reflectances obtained in the infrared field with a predetermined range of reflectances. If the spectrometer determines that the reflectances for each reagent fall with the corresponding predetermined range, the strip can be read and results can be processed. If the reflectances for any reagent, however, fall outside of the corresponding predetermined range, it has been discovered that this indicates that the strip has been improperly placed in the spectrometer. An improperly placed strip will cause an error to be reported and the test to be terminated.

An example of a reflectance spectrometer that is able to detect a misplaced strip is the CLINITEK® 50 and the CLINITEK® 500. An example of the diagnostic test strip used in accordance with this instrument is the MULTISTIX® reagent strip commercially available from Bayer Corporation. The CLINITEK® instrument and the MULTISTIX® strip are described in U.S. Pat. No. 5,945,341 and shown in FIGS. 1-4, as described in detail below.

Figure 2:
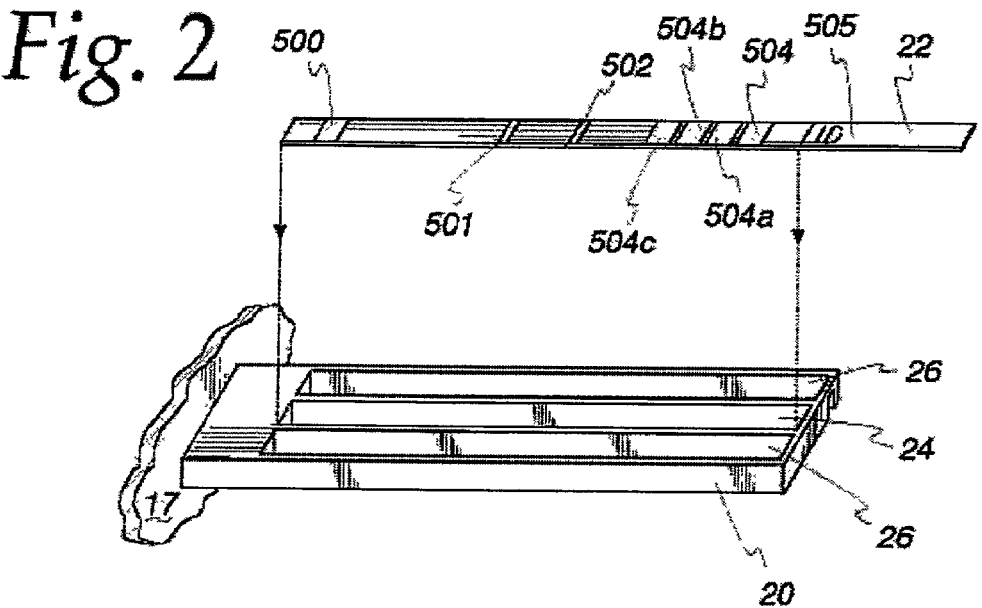
FIG. 2 is a perspective view of a diagnostic test strip and a feed table used with the spectrometer of FIG. 1.

FIG. 1 illustrates a reflectance spectrometer 10 for performing various tests, such as urinalysis tests, on a diagnostic test strip such as a reagent chemistry strip or an immunochemistry strip. The spectrometer 10 has an integral keyboard 12 with a number of entry keys 14 that may be depressed by the user. A visual display 16 for displaying various messages relating to the operation of the spectrometer 10 is disposed above the keyboard 12. Referring to FIGS. 1 and 2, the spectrometer 10 has a front face 17 with an opening 18 formed therein in which a feed table 20 for carrying a diagnostic test strip 22 is retractably disposed. The feed table 20 has a central channel 24 and two side channels 26 formed therein. The central channel 24 is sized to conform to the shape of the diagnostic test strip 22.

Figure 3:
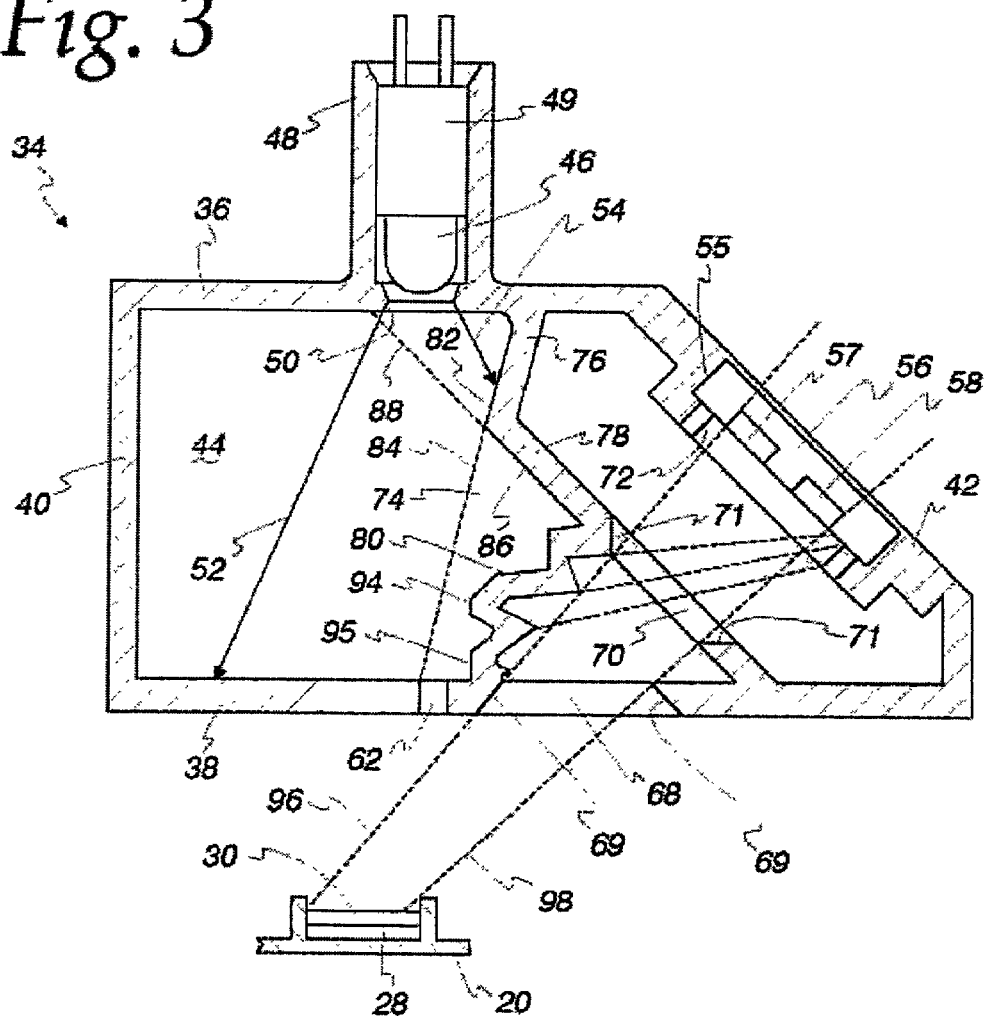
FIG. 3 is a cross-sectional view of a read head suitable for use in the spectrometer of FIG. 1.

The diagnostic test strip 22, as shown in FIG. 2, has a thin, non-reactive substrate 28 on which are laid a number of reagent pads 30, as shown in FIG. 3. The reagent pads 30 are composed of relatively absorbent layers of material that are impregnated with a respective reagent in specific locations referred to herein as test fields. Each test field is associated with a particular test to be performed. When each test field comes into contact with a urine sample, the reagent pad 30 changes color over a period of time depending on the reagent used and the characteristics of the urine sample. The color change, which is readable by the spectrometer 10, takes place as an indication of the presence and/or concentration of analyte in the fluid test sample.

To carry out an analysis of a liquid test sample, such as a urinalysis, the end of the diagnostic test strip 22 is dipped into a urine sample up to the test field 500. The test strip 22 is immersed in the liquid test sample so that all of the test fields are immersed in the liquid test sample, such as urine. The liquid migrates up the diagnostic test strip 22 due to the absorbent nature of the reagent pads 30 to cause a color change in stripe 502. Stripe 502 is a control stripe that changes color if sufficient sample volume is detected. The diagnostic test strip 22 may be, for example, a MULTISTIX® reagent strip commercially available from Bayer Corporation.

After the diagnostic test strip 22 is dipped in urine, the side of the diagnostic test strip 22 is blotted to remove excess urine. The diagnostic test strip 22 is then placed in the central channel 24 of the spectrometer feed table 20. The operator presses one of the entry keys 14 to initiate the testing. Pressing one of the entry keys 14 causes the tray 20 to be retracted into the spectrometer 10. It is contemplated in accordance with the present invention that the spectrometer may have an automated retracting tray that would retract into the spectrometer automatically after a strip is placed on the tray. The strip 22 may bear a visually readable strip identification 505 as its label. After the diagnostic test strip 22 is retracted into the spectrometer 10, the apparatus may need to measure some portions of the strip if extremely time-sensitive readings are needed for any test strip that is placed in the device. Then, the instrument positions a test strip 22 relative to a read head 34, shown in FIG. 3, at the location of the spectral identification (ID) marker field 504 and determines the spectral signature by analysis of the spectral reflectance values. In one embodiment of the present invention, the spectral ID marker field 504 is white and the spectrometer 10 is preprogrammed to read this as representing a conventional dry phase chemistry reagent strip. Another color could be used to inform the spectrometer 10 that a different reagent system, e.g., immunochromatographic, was being used on that test strip. This serves the purpose of automatically analyzing the strip in the proper way and generating a proper report. The instrument can be programmed to read the other marker fields, e.g., 504a, 504b, 504c, to correlate the sequence of reflected wavelengths with preprogrammed information regarding the test strip 22.

After the color coding sequence has been identified, the instrument 10 will move the test strip to the test fields, e.g., 500, 501. As explained in detail below, tests are performed on each of the test fields by illuminating a portion of the test field with white light from a light source and then determining the amount of reflectance from the test field based on the detection of light received from the illuminated portion of the test field at an angle (e.g., 45°) from the upper surface of the test strips. After each test is performed, the spectrometer feed table 20 is repositioned relative to an illumination source 46 so that the next test field to be tested is illuminated. When the testing is completed, the spectrometer 10 generates a record of the results, which are displayed on the visual display 16, printed on a strip of paper 32 (as shown in FIG. 1), and/or sent to a computer.

The steps of illuminating a portion of the diagnostic test strip and detecting the wavelength of the reflected light are accomplished by an optical system in the form of a read head 34. A read head 34 is used to illuminate portions of the test fields and for detecting light from the test fields and a portion of the spectrometer feed table 20 on which the diagnostic test strip 22 is disposed. U.S. Pat. Nos. 5,945,341 and 5,661,563 describe a read head suitable for use in the present invention and are hereby incorporated by reference in their entirety.

FIG. 3 is a cross-sectional view of an optical system in the form of a read head 34 for illuminating portions of the reagent pads 30 and for detecting light from the reagent pads 30 and a portion of the spectrometer feed table 20 on which the diagnostic test strip 22 is disposed. Referring to FIG. 3, the read head 34 has a housing with a top wall 36, a bottom wall 38, a side wall 40, an angled wall 42, a planar back wall 44, and a planar front wall (not shown) parallel to the back wall 44. An illumination source, such as a light bulb 46, is supported directly above the reagent pad 30 to be tested via a cylindrical housing portion 48 integrally formed with the top wall 36. When manufactured, the bulb 46 is dynamically fitted to a ceramic base 49 to ensure that the axial direction in which the bulb 46 emits light is substantially parallel to the longitudinal axis of the ceramic base 49. The bulb 46 emits light through a circular aperture 50 formed in the top wall 36 to form a cone of light defined by a first edge ray 52 and a second edge ray 54.

The angled side wall 42 has a rectangular aperture 55 formed therein in which a rectangular detector array 56 is disposed. The detector array 56 has four reflectance detectors 57, 58, 59, 60 disposed therein (see FIG. 4), each of which is composed of a conventional colored or infrared filter and a conventional silicon detector. Each filter allows light having a distinct wavelength to pass through so that each of the four detectors 57-60 is responsive to light of a different wavelength range. The four wavelength bands of the filters are 400-510 nanometers ("nm") (blue), 511-586 nm (green), 587-660 nm (red), and 825-855 nm (infrared or "IR"). Depending on the type of test being performed, one or more of the detectors 57-60 may be used.

Figure 4:
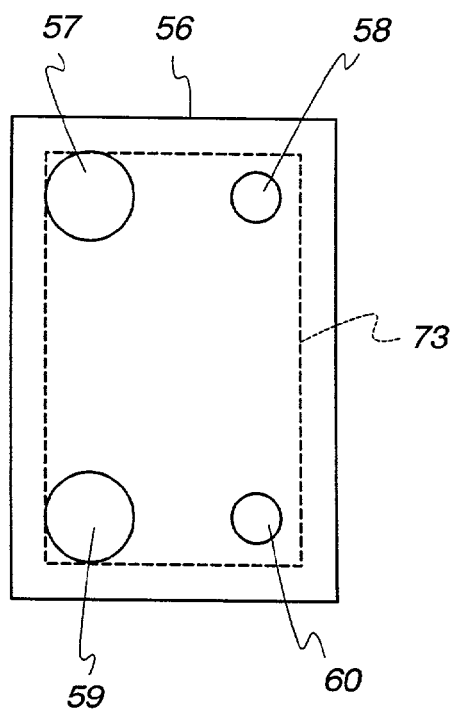
FIG. 4 is a schematic of a detector element/detector array useful in the spectrometer of FIG. 1.

The read head 34 operates by allowing light to pass through a first optical path from the light bulb 46 and through a relatively small rectangular aperture 62 formed in the bottom wall 38 to illuminate a relatively small rectangular area of the reagent pad 30 being tested. The reagent pad 30 may be moved relative to the aperture 62 so that different rectangular areas of the reagent pad 30 are illuminated. Light passes through a second optical path from the illuminated area on the reagent pad 30 through a first rectangular detection aperture 68 having angled edges 69 formed in the bottom wall 38, through a second rectangular detection aperture 70 having angled edges 71, and through a rectangular aperture 72 formed in the angled wall 42 to a detection area 73, as shown in FIG. 4, in which the four detectors 57-60 are disposed.

The interior of the read head 34 is provided with an irregularly shaped baffle 74 composed of a first planar wall segment 76, a second planar wall segment 78, and a zigzag shaped wall segment 80. The shape of the baffle 74 is designed to prevent singly-reflected light rays from reaching the reagent pad 30 from the light bulb 46 and to prevent singly-reflected light rays from reaching the detector area 73 from the reagent pad 30.

The misplacement of a diagnostic test strip 22 on the feed table 20 within the spectrometer 10 such as a strip that is tilted when inserted (instead of lying flat against the surface of the tray) or a strip that is incompletely inserted into the feed table 20, can be detected by setting maximum (upper) and minimum (lower) reference limits on the infrared readings obtained from reagents being tested in one or more test fields on the diagnostic test strip 22. The reagents that can be used for this purpose have reflectance values that do not change in the infrared region with variations in the reagent concentration. When the infrared readings obtained from these reagents do not fall between the upper and lower reference limits set on the infrared readings, the spectrometer 10 detects an error and results are not output by the spectrometer 10. Examples of suitable reagents that can be used to detect a misplaced diagnostic test strip include, but are not limited to, glucose, albumin and leukocyte.

Many persons skilled in the art would not realize that the IR reading for several of the reagents used herein (e.g., leukocyte, albumin, glucose) does not change due to concentration. Furthermore, it is not apparent that the IR reading of reagent areas such as glucose, albumin and leukocyte would be sensitive to minimal amounts of test strip misplacement due to tilting or incomplete insertion.

Referring to FIG. 3, infrared reflectance readings can be used to detect the misplacement of a diagnostic test strip 22 on the feed table 20 within the spectrometer 10. As 30 light from the bulb 46 is emitted and passes through aperture 62 to illuminate the reagent pad 30 being tested, light is reflected up to reflectance detector 57 to produce an infrared reflectance reading based upon the reagent being tested. When the diagnostic test strip 22 has been positioned correctly on the spectrometer feed table 20, light is reflected up to the reflectance detector 57 and the resulting infrared reading falls within the predetermined upper and lower reference limits. When the diagnostic test strip 22 is tilted to the right of center on the spectrometer feed table 20, an insufficient amount of infrared light is reflected up to the reflectance detector 57. Consequently, the resulting infrared reading is lower than the predetermined limit, the spectrometer 10 detects an error and the test is aborted. When the diagnostic test strip is tilted to the left of center on the spectrometer feed table 20, too much infrared light is reflected up to the reflectance detector 57. Consequently, the resulting infrared reading is higher than the predetermined limit, the spectrometer 10 detects an error and the test is aborted.

Specifically, the spectrometer will detect an error and abort the test if the IR readings of one or more reagents do not fall within a predetermined range of limits for each reagent. In one embodiment, an infrared reflectance reading is taken, for control purposes, of the reagent pad at the tip of the diagnostic test strip and of the reagent pads in the locations where the glucose, albumin and leukocyte reagents are located. The spectrometer 10 then compares the infrared reflectance readings that have been obtained with the predetermined limits to determine if a misplacement of the diagnostic test strip 22 has occurred. If one or more of the infrared limits have been violated, the spectrometer 10 displays an error and the test is aborted.

A tolerance of 0.015" has been created into each side of the feed table 20 such that the width of the central channel 24 of the feed table 20 amounts to the width of the test strip 22 plus an additional 0.015" on each side of the strip. Thus, if the strip is placed more than 0.015" to the left or right of the location in which a centrally-placed strip would generally be placed, a portion of the strip will rest on one of the side walls of the feed table 20. It has been determined that a strip that is placed more than 0.005" of the tolerance either to the right or the left of a central test strip location that allows 0.015" on either side of the test strip (i.e., the strip is misplaced more than 0.020" from a central location), the resulting IR percent reflectance reading will be outside the predetermined limits. If the spectrometer tests a strip with an IR reading that is outside of these acceptable limits, the spectrometer will abort the test. It is contemplated in accordance with the present invention that the use of different spectrometers and different feed tables will result in different acceptable predetermined limits.

In one embodiment, the predetermined or preset limit on the infrared reflectance readings is the distance that the test strip can be misplaced away from the central location on the feed table. The distance that the test strip can be misplaced away from the central location on the feed table for one embodiment of the present invention is 0.020". If a test strip is placed outside of this location (i.e., the strip is placed more than 0.020" from a central location on the feed table), the test strip has the possibility of being be improperly identified. Where the diagnostic test strip 22 is misplaced (or tilted) to the right, the infrared reflectance reading falls below the minimum predetermined limit. Where the diagnostic test strip 22 is tilted to the left, the infrared reflectance reading is greater than the maximum predetermined limit. In either situation, the resulting infrared reading falls outside of the predetermined limits, the spectrometer 10 detects an error and the test is aborted.

The spectrometer will also detect an error and abort the test if the test strip is incompletely inserted into the feed table 20. In one embodiment of the present invention, it has been determined that if a test strip is incompletely inserted by more than 0.050", the strip will likely be misidentified and incorrect outcomes will result. Specifically, when a test strip is incompletely inserted into the feed table 20, the detector within the read head 34 "sees" either a portion of the test strip between the pads or the detector sees a portion of the feed table. If the test strip is incorrectly inserted such that the read head sees the white backing of the test strip, the percent reflectance will be higher than the maximum predetermined limit for the predetermined reagents, as described in detail above. In this situation, the spectrometer will detect an error and the test will be aborted.

If the test strip is incorrectly inserted such that the read head sees or reads a portion of the black feed table 20, the percent reflectance will be lower than the minimum predetermined limit for the predetermined reagents, as described in detail above. In this situation, the spectrometer will detect an error and the test will be aborted.

Referring to FIG. 3, all surfaces of the baffle 74 and all interior surfaces of the housing walls 36, 38, 40, 42, 44 are shiny, specular surfaces so that any light incident upon any surface at an angle of incidence is reflected from that surface at an angle of reflection equal to the angle of incidence. This may be accomplished by injection-molding the read head 34 from a metal mold having highly polished molding surfaces. The read head 34 is preferably formed of black plastic so that only a small percentage of light, e.g. 5%, incident upon any of its internal surfaces is reflected. Consequently, any light that undergoes at least two reflections from any interior surfaces of the read head 34 is attenuated by at least 99.75%.

Referring to FIG. 3, the wall segment 76 has a specular surface 82 that is angled in a direction indicated by a dotted line 84 that intersects the bottom wall 38 at a point just to the left of the aperture 62. Consequently, any light rays emitted by the bulb 46 that impinge upon the surface 82 are reflected to an area to the left of the aperture 62. It should be noted that any such rays are reflected two or more times before they can pass through the aperture 62. It should also be noted that no light can be reflected from the surface 82 and pass directly through the aperture 62 without further reflection since the surface 82 is not visible when the interior of the read head 34 is viewed from the aperture 62.

The wall segment 78 has a specular surface 86 angled in a direction indicated by a dotted line 88 that intersects the top wall 36 at a point to the left of the circular opening 50 through which light passes. Consequently, there is no direct path from the light bulb 46 to the surface 86; therefore, any light that is reflected from the surface 86 to the aperture 62 will have undergone at least two reflections from the interior surfaces of the read head 34.

Figure 3A:
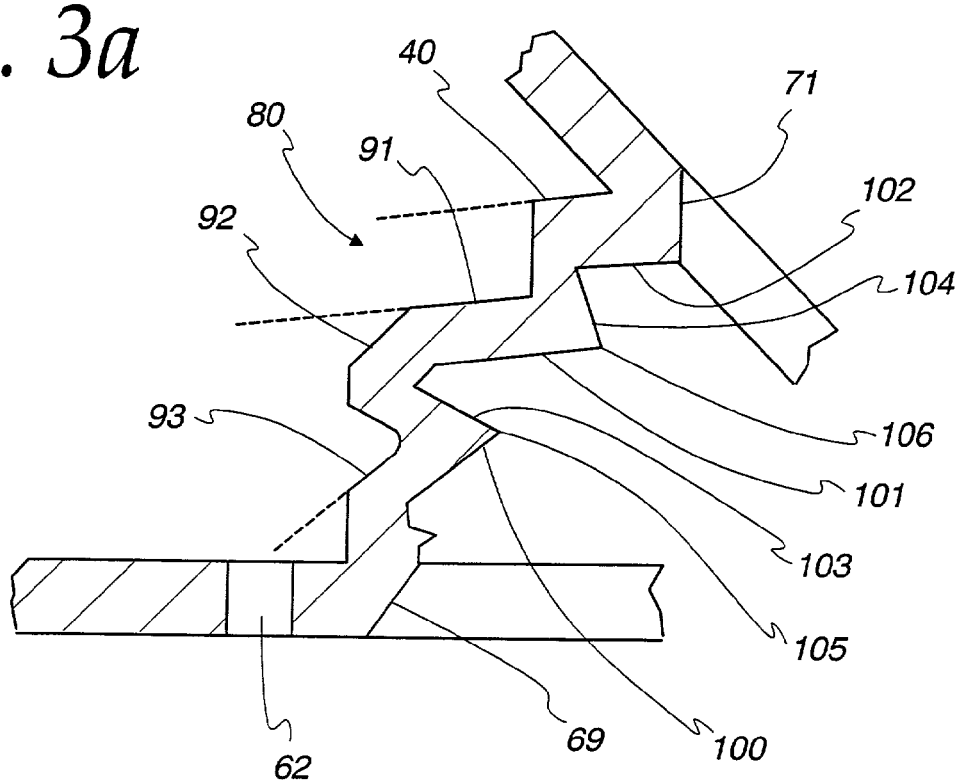
FIG. 3a is an enlarged view of a portion of the read head shown in FIG. 3.

Referring to FIG. 3a, the zigzag wall segment 80 has angled surfaces 91-93, each of which is angled in a direction indicated by a respective dotted line. Since all of the dotted lines intersect the bottom wall 38 or the side wall 40 to the left of the aperture 62, no light that impinges upon these surfaces 91-93 directly from the light bulb 46 can be reflected directly to the aperture 62. The zigzag wall segment 80 has two further surfaces 94, 95, as shown in FIG. 3, that are angled so that any light that impinges on those surfaces directly from the bulb 46 is reflected exclusively to the area of the bottom wall 38 to the right side of the aperture 62.

The only surfaces from which light rays emitted by the bulb 46 can be singly reflected and still pass through the aperture 62 are the vertical walls of the aperture itself. However, such singly reflected light rays constitute an insignificant amount of the total light which passes directly from the light bulb 46 to the walls 40 or 44 to the aperture 62. However, since the bulb concentrates light in a forward direction within the cone defined by rays 52 and 54, the amount of light going through the aperture 62 from this path is insignificant.

The second optical path from the reagent strip 22 to the detector area 73, is generally indicated by a pair of dotted lines 96 and 98, as shown in FIG. 3. The side of the zigzag wall segment 80 which is disposed adjacent to the second optical path has a plurality of planar, specular surfaces 100, 101 and 102 which are angled in a direction indicated by a number of corresponding dotted lines, as shown in FIGS. 3a, that intersect the angled side wall 42 at a point to the lower right of the detector area 73. Consequently, any light rays that impinge upon these surfaces 100-102 directly from the reagent strip 22 without reflection cannot reach the detector area 73 without at least one more reflection, and any such light rays will be attenuated by at least 99.75%. The wall surfaces 100 and 103 join at an edge 105 and the wall surfaces 101 and 104 join at an edge 106 with the edges 105 and 106 being substantially aligned with a respective edge of the detection area 73. The edges 69 and 71 of the detection apertures 68 and 70 are aligned with the edges of the detection area 73. In general, the instrument detects light having a specific wavelength range. When the range includes visible wavelengths in the range of 400 to 700 nm, a color is assigned to the filter. When the filter does not transmit any visible wavelengths, such as in the case where infrared radiation is used, the concept of color does not apply.

Figure 5:
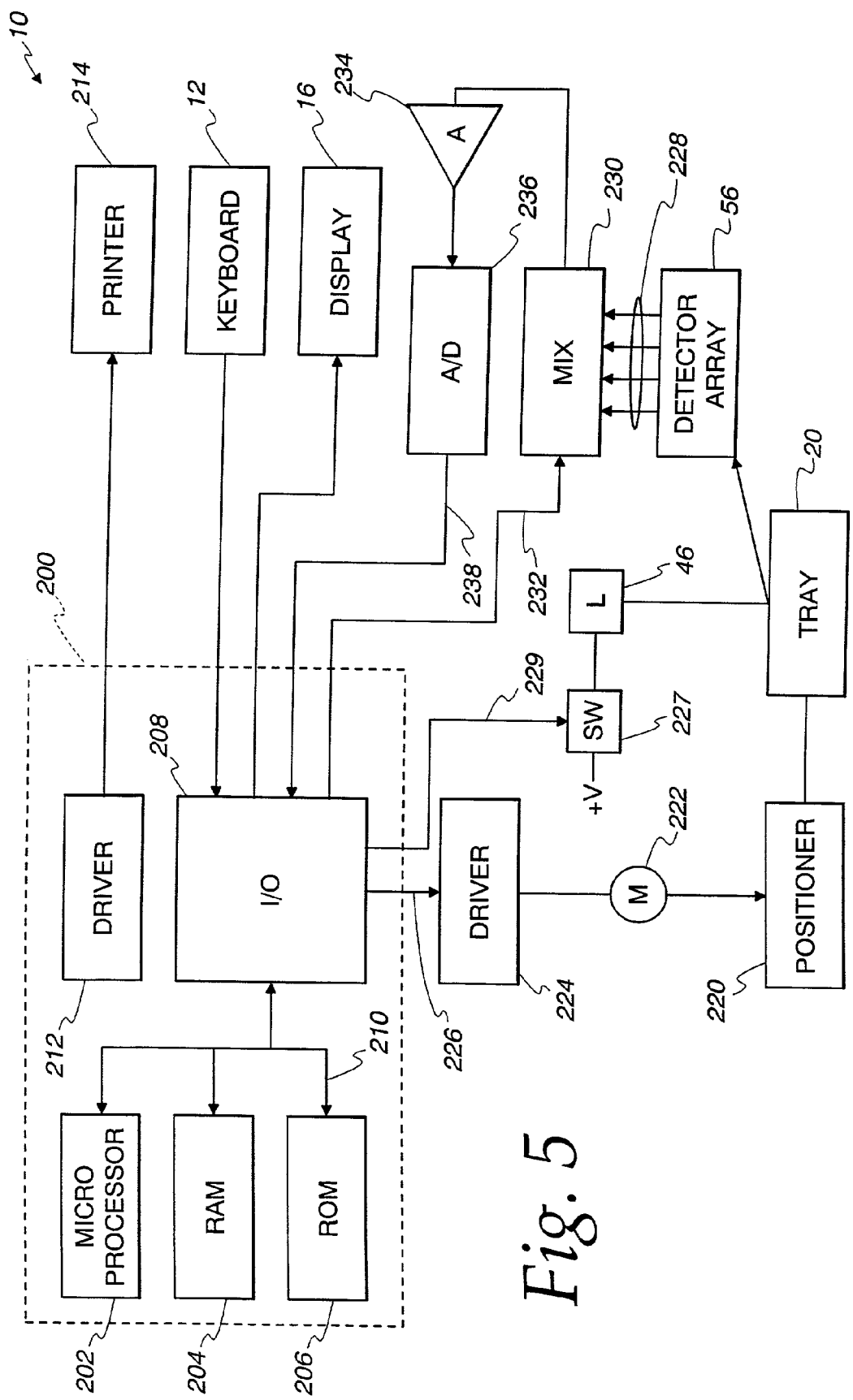
FIG. 5 is a block diagram of the electronics of the spectrometer of FIG. 1.

FIG. 5 is a block diagram of the electronics and other components of the spectrometer 10. The details of the operation of the spectrophotometer are described in U.S. Pat. No. 5,945,341, which is hereby incorporated by reference in its entirety. Referring to FIG. 5, the operation of the spectrometer is controlled by a microcontroller 200 that has a microprocessor 202, a random access memory (RAM) 204, a read only memory (ROM) 206 and an input/output (I/O) circuit 208 all of which are interconnected with an address/data bus 210. As schematically shown in FIG. 5, the operation of the spectrometer 10 is controlled by a computer program stored in the ROM 206 and executed by the microprocessor 202. The microcontroller 200, which may be a conventional microcontroller such as a DS2253T microcontroller commercially available from Dallas Semiconductor, can incorporate a driver circuit 212 connected to the I/O circuit 208 for driving a printer 214.

The microcontroller 200 controls the movement of the reagent strip feed table 20 via a conventional positioner 220 mechanically coupled to the feed table 20 and a motor 222 that is typically a stepping motor driven by drive signals generated by a driving circuit 224 connected to the I/O circuit 208 via an electrical line 226.

The microcontroller 200 selectively turns on the light bulb 46 via a switch 227 connected to the I/O circuit 208 via an electrical line 229. The light bulb 46 is turned on one second before the performance of the test so that it will be sufficiently warmed up.

Each of the detectors 57-60 of the detector array 56 generates an electrical reflectance signal on one of a number of electrical lines 228. Each reflectance signal has a magnitude that depends on the amount of light detected by the associated detector. The microcontroller 200 can selectively read any one of the reflectance signals by transmitting a select signal to a multiplexer 230 via a line 232. The multiplexer 230 then transmits the selected reflectance signal to an amplifier 234 and an analog-to-digital (A/D) converter 236 that transmits the binary signal output by the amplifier 234 to the microcontroller 200 via a line 238 connected to the I/O circuit 208. The microcomputer analyzes the binary data from the A/D converter by processing the data through the appropriate algorithm. It then generates a report that is transmitted according to previous instructions from the operator.

Figure 6:
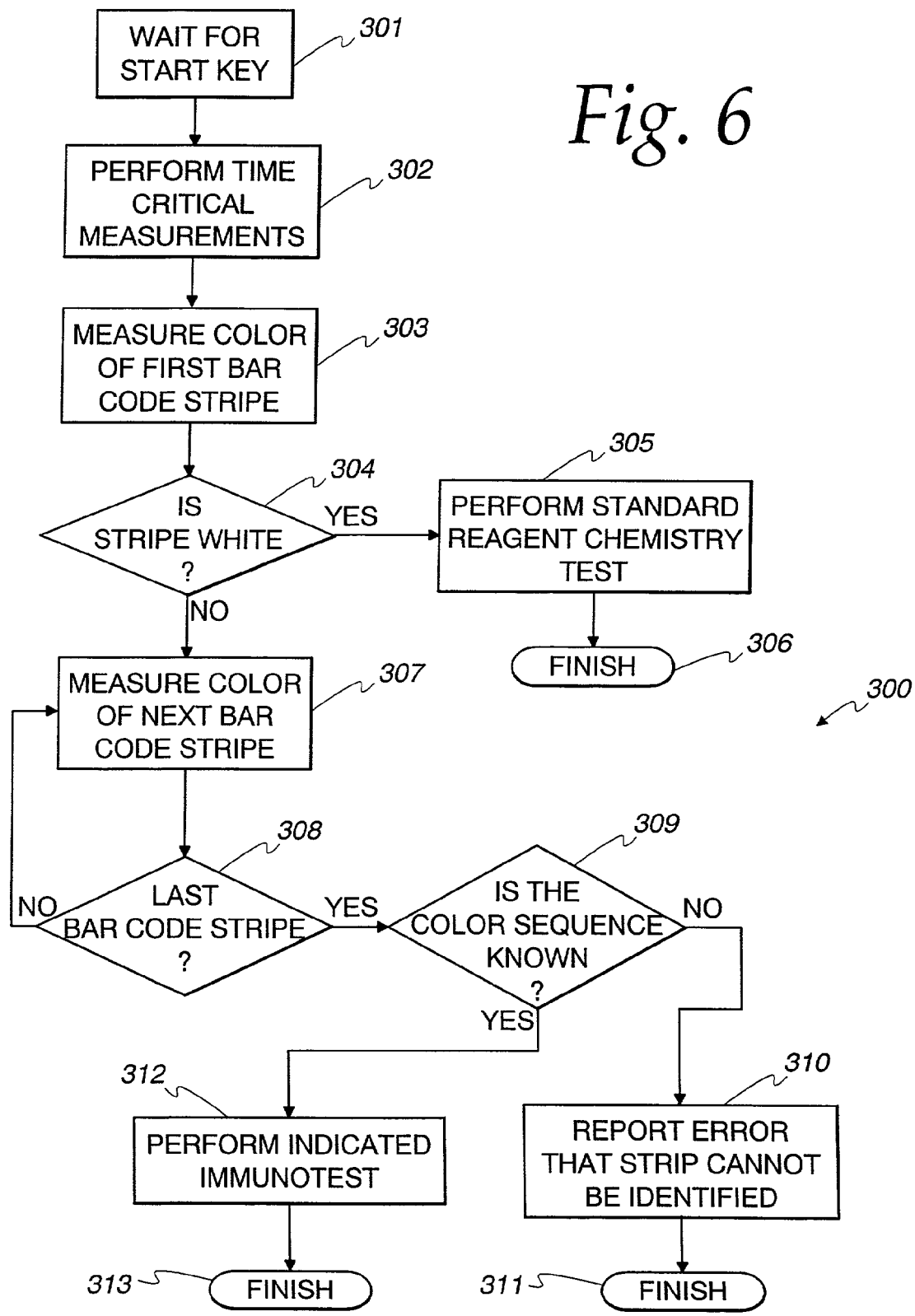
FIG. 6 is a flowchart of a computer program routine that may be used to correlate the spectral reflectance values of the reagent pads with preprogrammed information concerning the diagnostic test strip. The series of reagent pads define specific unique color sequences for the information concerning the diagnostic test strip.

FIG. 6 is a flowchart of a computer program routine that may be used to correlate the spectral reflectance values of the reagent pads with preprogrammed information concerning the diagnostic test strip. The series of reagent pads define specific unique color sequences for the information concerning the diagnostic test strip. The user signals, in step 301, the M spectrometer 10 that a diagnostic test strip 22 is ready to be placed in the spectrometer feed table 20 by pressing the start key 14. The microprocessor waits until this signal is detected.

Because some test strips possess test fields that must be analyzed very quickly, insufficient time exists for the marker fields to be read before the test field is evaluated. For example, in the analysis of some analytes, such as leukocytes, the chemistry reacts so quickly that if the device were to wait to take the first reading for the analyte until after reading the bar code, the reading would occur too late. Accordingly, the leukocyte position is always read first even if it turns out that the strip has no leukocyte reagent. In this event, step 302 requires positioning the feed table 20 relative to the read head 34 in order to take all required reflectance measurements from the test strip beginning with the test field and followed by the reading of the marker fields. If it is later determined that measurements of the reflectance from the test fields is not required, such as in the case where the system is reading an immunotest strip, these measurements can be discarded.

At step 303, the spectrometer 10 positions the feed table 20 relative to the read head 34 at the first marker field 504 that can be depicted as reflecting blue wavelengths. The amount of light sensed by the detectors is proportional to the amount of light reflected from the color bar (marker field) at the various wavelengths. For example, if the amount of reflected light is above 85% in the red and in the green and in the blue, the spectrometer would determine the color of the marker field to be white. The color coding system of the present invention can be used to communicate information concerning tests that can be performed by traditional dry chemical reagent strips or immunochromatographic strips. Thus, in a preferred embodiment of the present invention, the spectrometer is programmed to recognize that a traditional dry chemical reagent strip is being viewed when marker field 504 is white. In this case (i.e., if the reagent strip is white), at step 304 the software will branch to step 305 and perform a standard reagent chemistry test using, for example, a MULTISTIX® 10 SG reagent test strip from Bayer Corporation. The test concludes at step 306.

At step 304, if the spectrometer determines that the color of the first bar 504 is not white, but some other color such as blue, green, black or red, then at step 307 the spectrometer will position the tray relative to the read head at the next bar 504*a* and measure the color of the bar 504*a*. At step 308, the spectrometer determines that there are more color bars to read by reaching the maximum number of bars or recognizing a specific short sequence as the bars are read. For example, if the bar is white, there is only one bar in the sequence. If there are more colored bars to read, the software loops to step 307 and positions the tray relative to the read head at the next colored bar and measures its color. This step is repeated for each of the colored bars on the strip. At step 308, if the spectrometer determines that there are no more color coding bars to read, the software loops to step 309.

At step 309, if the spectrometer determines that the color sequence does not correspond to any known test strip, the software branches to step 310, reports an error and concludes at step 311. If the color sequence does correspond to a known color sequence and thus, a known test strip, as correlated with the preprogrammed information at step 309, the software branches to step 312, performs the indicated immunotest and then the test concludes at step 313.

Figure 7:
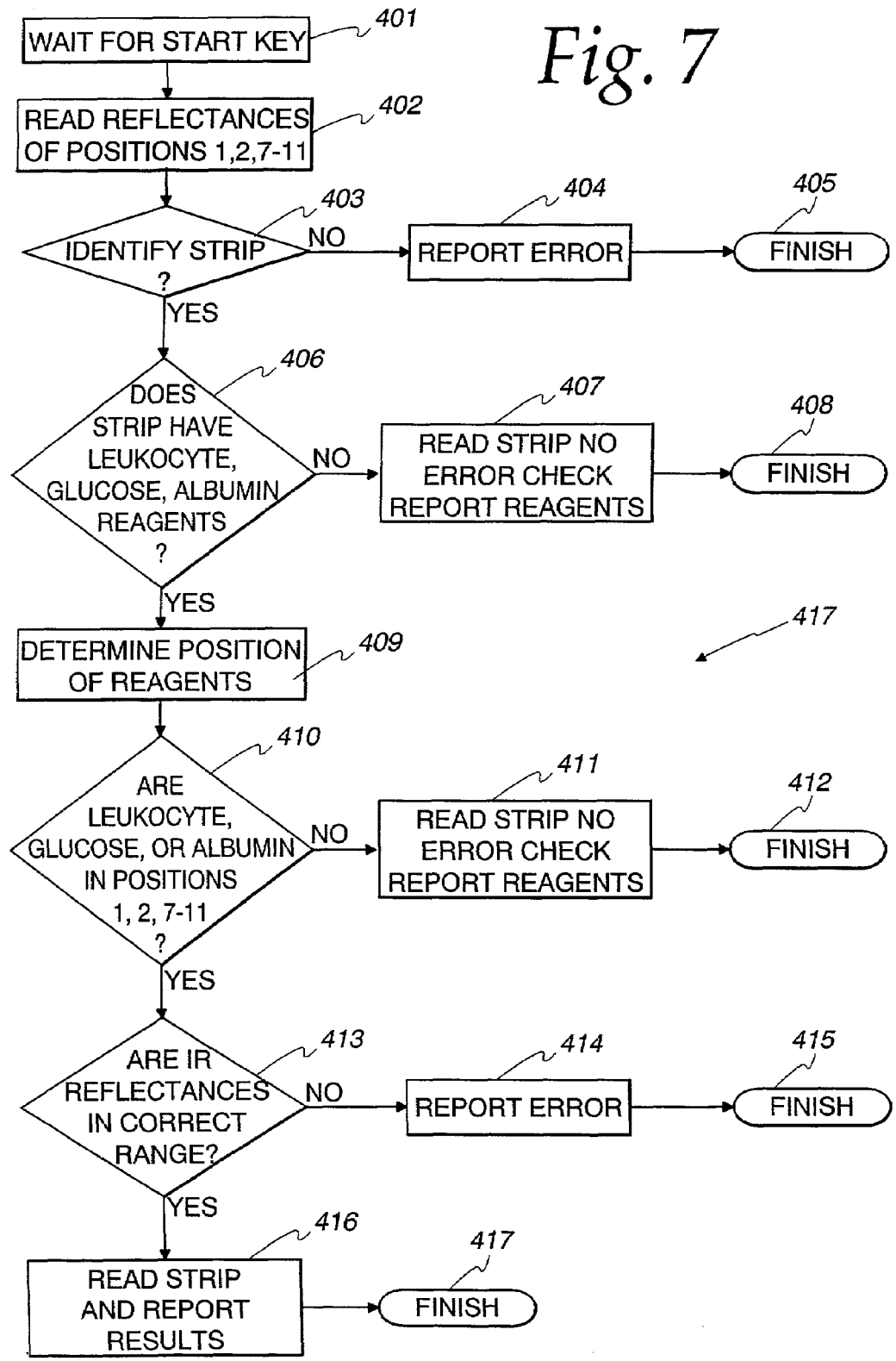
FIG. 7 is a flowchart relating to the detection of a misplacement of the diagnostic test strip by determining the presence and position of several reagents and comparing the infrared reflectances of such reagents to predetermined ranges.

A flowchart that relates to the detection of a misplacement of the diagnostic test strip is shown in FIG. 7. Referring now to FIG. 7, after a start key is pressed at step 401, the reflectances of positions 1, 2, and 7-11 of the test strip are then read at step 402. If the spectrometer 10 is not able to determine the reflectances, and, thus, identify the test strip at step 403, an error is reported at step 404 and the test concludes at step 405. If the spectrometer 10 is able to identify the test strip at step 403, the spectrometer determines, at step 406, if the strip has, for example, leukocyte, glucose or albumin reagents. If the spectrometer determines that the strip does not have any of the reagents that will allow the spectrometer to determine if the strip is improperly inserted (e.g., leukocyte, glucose or albumin), the strip is read, no error check is performed and the reagents are reported at step 407. This test concludes at step 408. It is contemplated in accordance with the present invention that other reagents could be used to detect a misplaced strip so long as the IR reflectances can be interpreted in a manner consistent with the present invention.

If it is determined that the strip does have the aforementioned reagents at step 406, the position of the reagents is determined at step 409. At step 410, the spectrometer determines if leukocyte, glucose or albumin are present on the test strip. If these reagents are not in the appropriate positions on the strip, the strip is read, no error check is performed and the reagents are reported at step 411 and the test concludes at step 412. If it is determined that leukocyte, glucose or albumin is located on the test strip, the spectrometer must determine, in step 413, if the IR reflectances are in the correct range. If not, an error is reported at step 414 and the test concludes at step 415. If the IR reflectances of leukocyte, glucose or albumin are in the correct predetermined range as determined in step 413, the test strip is read and the results are reported at step 416 and the test concludes at step 417.

The following example is presented to illustrate various embodiments of the invention. All numerical values are approximate numbers. The specific details within this example should not be construed to limit the invention as otherwise described and claimed herein. The following example shows that the use of the IR reflectances of several reagents prevents misidentifications.

The CLINITEK® 50, the instrument used to perform the tests in the following example, has the ability to read diffuse reflectances in the blue, green, red and IR spectral regions. The instrument also has the ability to position any relevant region of the strip relative to the optical system, thus measuring the reflectance values for each of the four ID band positions in the blue, green, red and IR regions. These reflectance values are referred to herein as spectral intensities or spectral diffuse reflectance values because they are the reflectance values as a function of wavelength. In this case, intensity refers to the magnitude of the diffuse reflectance signal.

In actual operation, the user may want to analyze a diagnostic test strip 22, as shown in FIG. 2, for a particular substance. The user dips the test strip 22 into a sample of urine up to the indicated level 500 for a predetermined time, such as thirty (30) seconds. The strip is then withdrawn from the sample. While the same is being withdrawn, a start key 12 of the instrument 10, in FIG. 1, is pressed. The strip is placed on the table 20 within ten (10) seconds.

The instrument homes the table, measures the reflectance of the calibration chip on the table 20 and positions the reagent pad under the read head 34 as determined by the selected type of multiple reagent test strip. An initial read of the reagent pad is made at an initial time in case it is determined by reading the color-coded marker sequence that a multiple reagent test strip has been placed in the instrument. This is done because reading the initial reflectance value of the pad after reading a marker field will delay reading the pad beyond the time required for the initial reading of the pad. In this example, a strip with a pad designed for detecting leukocytes is used. If it is later determined that there is no leukocyte pad, this initial reading is discarded. The instrument 10 proceeds to position the test strip 22 with marker field 504 under the read head 34.

EXAMPLE

IR readings were taken from the tip pad and several other pads of the test strip after retraction into the CLINITEK® 50 spectrometer. After the strip is analyzed for the presence or absence of a color band, the instrument compared the IR readings at the positions of the expected white blood cell (leukocyte), glucose and albumin pads to the predetermined reference test limits to determine if a misidentification occurred (i.e., if the strip has been incorrectly placed into the table, either tilted or incompletely inserted into the table). If one or more IR reference limits were violated, an error was displayed and the test was aborted.

The minimum and maximum IR reflectances were obtained from a CLINITEK® 50 on nine (9) reagents correctly laid in the feed table of the spectrometer. The maximum reflectances were generally obtained in water and are reflected in Table I. The minimum reflectances included solutions up to the concentrations listed in the table below.

TABLE I

| Reagent | Maximum % IR Reflectance | Solution | Minimum % IR Reflectance | Solution | % Reflectance Obtained when Strip Placed 0.020"-0.060" Right of Center | % Reflectance Obtained when Strip Placed 0.040"-0.072" Left of Center |
|---|---|---|---|---|---|---|
| White Blood Cell (Leukocyte) | 70.3 | Water | 60.0 | Up to 1000 cells/uL | 42.8-50.8 | 53.6-78.4 |
| Glucose | 86.7 | Water | 79.7 | Up to 5000 mg/dL | 53.0-63.0 | 96.2-103.0 |
| Bilirubin | 71.3 | Water | 61.2 | Up to 100 mg/dL | 44.0-55.3 | 70.1-88.7 |
| Specific Gravity | 72.6 | Water | 66.0 | Up to 1.040 | 42.6-54.8 | 67.7-80.3 |
| pH | 72.3 | Water | 65.8 | pH 4-10 | 43.2-53.7 | 67.6-87.6 |
| Protein | 70.9 | Water | 62.5 | Up to 2500 mg/dL | 45.2-54.4 | 66.0-82.9 |
| Nitrite | 75.4 | Water | 67.1 | Up to 10 mg/dL | 46.0-54.1 | 67.1-92.6 |
| Albumin | 71.7 | Water | 63.3 | Up to 2500 mg/dL | 45.4-54.2 | N/A |
| Ketone | 71.8 | Water | 47.8 | 300 mg/dL | 43.5-51.2 | 65.6-87.3 |

The sixth column of Table I lists the ranges of percent reflectances obtained when a water dipped strip was intentionally misplaced and tilted from 0.020" to 0.060" to the right of the correctly laid point on the feed table. The seventh column of the above table lists the ranges of percent reflectances obtained when a water dipped strip was intentionally misplaced and tilted from 0.040" to 0.072" to the left of the correctly laid point on the feed table. It is generally known that, due to the tolerance on the feed table, a misplacement of up to 0.015" is still considered flat and distortions or errors will not result from such a strip misplacing.

As shown in the table above, the percent reflectance of, for example, the glucose reagent when the strip is placed more than 0.020" to the right of a central location on the feed table is less than the minimum acceptable predetermined minimum. Similarly, the percent reflectance of the glucose reagent when the strip is placed more than 0.020" to the left of a central location on the feed table is greater than the minimum acceptable predetermined minimum. Thus, a spectrometer analyzing a test strip that is misplaced by more than 0.020" either to the right or left of a central location on the feed table will result in an aborted test.

As stated above, it has been discovered that the analysis of the IR reflectance for leukocyte, albumin and glucose will allow a user to easily and quickly determine if a test strip has been incorrectly or improperly inserted into the feed table of the spectrometer. It is conceivable that the test strip will be inserted in such a way that the spectrometer will analyze the percent IR reflectance in the three positions in which leukocyte, albumin and glucose should reside and for one or two of these three reagents described to fall within the predetermined ranges. However, it is virtually impossible for the spectrometer to analyze each of the three reagents and return a result with three correct readings of the IR reflectances. Thus, if the test strip is improperly tilted more than approximately 0.020", as described above, the spectrometer will abort the test.

While the invention has been described with respect to a number of limited embodiments, variations and modifications exist. Those skilled in the art will recognize that many changes may be made thereto without departing from the spirit and scope of the present invention. The appended claims intend to cover all such variations and modifications as falling in within the scope of the invention, which is set forth in the following claims:

What is claimed is:

1. A method of using an infrared reading to detect the misidentification of a diagnostic test strip having a plurality of marker fields configured to reflect light in a manner correlated to identification of the test strip, and having a plurality of test pads separate from said marker fields, said test pads having reagents thereon, said method comprising the steps of:
   identifying the test strip by reading reflectances of one or more of the plurality of marker fields;
   determining if the infrared reflectance of one or more of the plurality of test pads is within an acceptable predetermined range; and
   determining that the test strip is misidentified in the event said infrared reflectance of one or more of the plurality of test pads is outside of the acceptable predetermined range.

2. The method of claim 1, further comprising the step of aborting the test if said infrared reflectances are not within said range.

3. The method of claim 2 wherein said test will be aborted if said test strip is more than about 0.020" from a central location on a feed table or if said test strip is incompletely inserted by more than about 0.050".

4. The method of claim 1 wherein said reagents are leukocyte, glucose and albumin.

5. The method of claim 4 wherein said predetermined infrared reflectance range of said leukocyte reagent is from about 57.0 to about 73.0 percent infrared reflectance.

6. The method of claim 4 wherein predetermined infrared reflectance range of said glucose reagent is from about 75.0 to about 90.0 percent infrared reflectance.

7. The method of claim 4 wherein the predetermined range of said albumin reagent is from about 60.0 to about 75.0 percent infrared reflectance.

8. An automated method of using an infrared reading to detect the misidentification of a diagnostic test strip disposed on a feed table, the test strip having a plurality of marker fields configured to reflect light in a manner correlated to identification of the test strip, and having a plurality of test pads separate from said marker fields, said test pads having reagents thereon, said method comprising the steps of:

identifying the test strip by reading reflectances of one or more of the plurality of marker fields;

determining if said test strip possesses specified reagents on the plurality of test pads;

locating the position of plurality of test pads on said strip;

reading the infrared reflectances from each of the plurality of test pads;

determining if said infrared reflectances are within an acceptable predetermined range; and determining that said test strip is misidentified in the event said infrared reflectances are outside of the acceptable predetermined range.

9. The method of claim 8, further comprising the step of aborting said method if said infrared reflectances for one or more of said reagents are not within said predetermined range.

10. The method of claim 9 wherein said test will be aborted if said test strip is more than about 0.020" from a central location on said feed table or if said test strip is incompletely inserted by more than about 0.050".

11. The method of claim 8 wherein said reagents are leukocyte, glucose and albumin.

12. The method of claim 11 wherein said predetermined infrared reflectance range of said leukocyte reagent is from about 57.0 to about 73.0 percent infrared reflectance.

13. The method of claim 11 wherein predetermined infrared reflectance range of said glucose reagent is from about 75.0 to about 90.0 percent infrared reflectance.

14. The method of claim 11 wherein the predetermined infrared reflectance range of said albumin reagent is from about 60.0 to about 75.0 percent infrared reflectance.

15. An automated method of reading a test strip for the analysis of one or more analyte(s) in a liquid test sample that comprises the steps of:

a) providing a test strip having a plurality of tests fields on its surface that reflects light at a specific range of wavelengths and at least two distinct marker fields on the same surface of said test strip as said test fields, said marker fields reflecting light at different ranges of wavelengths from each other and from said test fields in a coded sequence of ranges of wavelengths, said coded sequence correlates to information concerning identification of the test strip;

b) introducing said test strip into a strip reading device equipped with reading means for both said test fields and said marker fields, said reading means comprises a light source as transmitter and a light sensitive element as receiver, said receiver being capable of differentiating between said ranges of wavelengths at which said test fields and said marker fields reflect, said strip reading device also being equipped with means for correlating the coded range of infrared wavelength sequence of reflected light with preprogrammed information concerning said test strip, said correlating means being in operative communication with a receiving means, said reading device having means for moving said test strip and said receiving means relative to one another so that the reflectance of said test fields and said marker fields can be individually read by said reading means;

c) allowing said ranges of wavelength values reflected by said test fields and said marker fields to be individually read by said reading means;

d) allowing said reading means to communicate said coded infrared sequence of spectral reflectance values reflected from said marker fields to said correlating means and allowing said correlating means to correlate said infrared sequence of reflected range of wavelength values with said preprogrammed information concerning said test strip;

e) allowing said reading means to communicate said reflected range of infrared wavelength values to said correlating means and allowing said correlating means to determine, for one or more of the reagents disposed on said test strip, if said reflected range of infrared wavelength values are within a predetermined range of infrared reflectances; and f) determining that said test strip is misidentified in the event said infrared reflectances from said test fields are outside of the predetermined range.

16. The method of claim 15 wherein said test strip is placed on a feed table.

17. The method of claim 15 wherein said reagents comprise leukocyte, glucose and albumin.

18. The method of claim 17 further comprising the step of aborting said method if said infrared reflectances for one or more of said reagents are not within said predetermined range.

19. The method of claim 18 wherein the predetermined infrared reflectance range for leukocyte is from about 57.0 to about 73.0 percent infrared reflectance.

20. The method of claim 18 wherein the predetermined infrared reflectance range for glucose is from about 75.0 to about 90.0 percent infrared reflectance.

21. The method of claim 18 wherein the predetermined infrared reflectance range for albumin is from about 60.0 to about 75.0 percent infrared reflectance.

22. The method of claim 15 wherein said test will be aborted if said test strip is more than about 0.020" from a central location on said feed table or if the test strip is incompletely inserted by more than about 0.050".

23. The method of claim 15 wherein said range of wavelength value reflected from said test fields and said marker fields are read by moving said test strip and said reading means relative to each other.

24. The method of claim 15 wherein said feed table is movable in relation to said reading means and wherein said test strip is placed on said feed table and moved relative to said reading means so that the reading means can scan the marker fields.

25. The method of claim 15 wherein said reading means is capable of acquiring spatial and spectral reflectances across the length of said test strip.

26. The method of claim 15 wherein said information concerning said test strip is calibration information based on the particular batch from which said test strip was obtained.

27. The method of claim 15 wherein said information concerning said test strip relates to location of reactive areas, critical times, strip age and strip reactivity.

28. The method of claim 15 in which said marker fields comprise bars that are substantially parallel to each other and are substantially perpendicular to the longitudinal axis of the test strip.

* * * * *